United States Patent [19]

Someno et al.

[11] Patent Number: 5,221,752
[45] Date of Patent: Jun. 22, 1993

[54] α-KETO AMIDE DERIVATIVES

[75] Inventors: Tetsuya Someno, Oumiya; Fumika Yamada, Tokyo; Hideo Sugimura, Tokyo; Yasuhiko Muraoka, Tokyo; Makoto Tsuda, Tokyo; Tomio Takeuchi, Tokyo; Takaaki Aoyagi, Fujisawa, all of Japan

[73] Assignee: Nippon Kayaku Kabushiki Kaisha, Tokyo, Japan

[21] Appl. No.: 729,419

[22] Filed: Jul. 12, 1991

[30] Foreign Application Priority Data

Jul. 27, 1990 [JP] Japan .................................. 2-197753
Mar. 1, 1991 [JP] Japan .................................. 3-057753

[51] Int. Cl.⁵ .......................................... C07D 207/08
[52] U.S. Cl. .................................... 548/540; 548/518
[58] Field of Search ................. 548/540, 518; 514/423

[56] References Cited

PUBLICATIONS

Toda, et al., C.A. 113:23894k (1989).
Henning, et al., C.A., 112:76705g (1989).
Igarashi, et al., C.A., 92:42341s (1979).

*Primary Examiner*—Joseph Paul Brust
*Attorney, Agent, or Firm*—Nields & Lemack

[57] ABSTRACT

The present invention discloses a new α-keto amide derivative or a salt thereof represented by the formula (1):

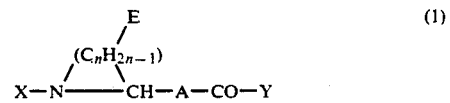

wherein X represents (1) a peptide residue or amino acid residue in which the functional group may be protected, (2) a hydrogen atom or (3) an amino-protective group, Y represents a peptide residue or amino acid residue in which the functional group may be protected, E represents a substituent on the alkylene ($C_nH_{2n-1}$) and is a halogen, lower alkoxy or hydrogen, A represents a carbonyl group or mono- or di-substituted methylene (the substituent being a hydroxy, lower alkoxy, phenylimino or benzylimino), and n represents an integer of 2 to 6.

The compound of the present invention is effective in inhibiting prolyl endopeptidase activity and useful as an active ingredient of an enzyme inhibitor.

3 Claims, No Drawings

α-KETO AMIDE DERIVATIVES

BACKGROUND OF THE INVENTION

Peptidyl aldehydes such as leupeptin, chymostatin and elastatinal are known as low-molecular enzyme inhibitors derived from natural substances. Various peptidyl aldehydes as the inhibitors are synthesized in the light of them. It is known that when the peptidyl aldehydes inhibit serine protease or thiol protease, they form a covalent bond with the hydroxyl group or thiol group of the enzyme [cf. Thompson, R. C., Biochemistry, 12, 47–51 (1973)].

Since peptidyl aldehydes have an aldehyde group at the C-terminus of the peptide chain, a change in the amino acid sequence conducted in order to improve the specificity with an enzyme is limited to the N-terminus thereof. Poststatin previously found by the inventors has an α-keto amide structure in the peptide chain. The inventors continued intensive investigations thereafter on compounds having an enzymatic specificity from these points of view.

These protease-inhibiting active substances are useful as the active ingredient expected to be clinically applicable for treating autoimmune diseases, for improving the circulation in the brain, and for treating amnesia.

SUMMARY OF THE INVENTION

The present invention relates to new peptides which are expected to have an activity of inhibiting proteases, particularly serine protease or thiol protease. Namely the present invention relates to new α-keto amide derivatives or salts thereof represented by the formula (1):

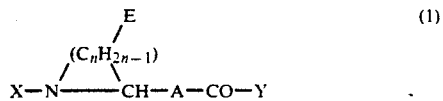

wherein X represents a peptide residue or amino acid residue in which the functional group may be protected, a hydrogen atom or an amino-protective group such as urethane or acyl, Y represents a peptide residue or amino acid residue in which the functional group may be protected, E represents a substituent on the alkylene $(C_nH_{2n-1})$ selected from among a halogen, lower alkoxy or hydrogen, A represents a carbonyl group or mono- or di-substituted methylene (the substituent being a hydroxy, lower alkoxy, phenylimino or benzylimino), and n represents an integer of 2 to 6.

The compounds synthesized according to the present invention exhibit an effect of inhibiting prolyl endopeptidase and are useful as an active ingredient of an enzyme inhibitor having an enzymatic specificity.

DETAILED DESCRIPTION OF THE INVENTION

The amino acid residue of X or Y or the amino acid residue constituting the peptide residue of X or Y in the formula (1) usually includes an α-amino acid residue but is not limited to the α-amino acid residue but it may be a β-amino acid such as β-alanine.

The α-amino acids include amino acids of the following formula (a) and those of the following formula (b):

wherein $R_2$ represents a hydrogen atom or a lower alkyl (i.e. a substituted or unsubstituted lower alkyl, the substituent being an amino, hydroxyl, mercapto, lower alkylthio, carboxyl, phenyl, hydroxyphenyl, imidazole or indolyl group), and

wherein $R_3$ represents a hydrogen atom or a hydroxyl group (if necessary to be protected).

Examples of the amino acids include glycine (Gly) ($R_2=H$), alanine (Ala) ($R_2=CH_3$), valine (Val) [$R_2=CH(CH_3)_2$], leucine (Leu) [$R_2=C_2H_3(CH_3)_2$], isoleucine (Ileu), serine (Ser) ($R_2=CH_2OH$), threonine (Thr) [$R_2=CH(OH)CH_3$], cysteine (CySH) ($R_2=CH_2SH$), methionine (Met) [$R_2=(CH_2)_2SCH_3$], aspartic acid (Asp) ($R_2=CH_2COOH$), glutamic acid (Glu) ($R=CH_2CH_2COOH$), lysine [$R_2=(CH_2)_4NH_2$], arginine (Arg) [$R_2=(CH_2)_3NHC(NH)NH_2$], phenylalanine (Phe) ($R_2=CH_2C_6H_5$), tyrosine (Tyr) ($R_2=CH_2C_6H_4OH$), histidine (His) ($R_2=$imidazolylmethyl), tryptophan (Try) ($R_2=$indolylmethyl), homophenylalanine (hPhe) ($R_2=CH_2CH_2C_6H_5$), proline (Pro) ($R_3=H$) and hydroxyproline (Hypro) ($R_3=OH$). These amino acids have any of D, L or DL configurations.

A preferred amino acid residue which may have a protected amino group in the X is valine (Val), proline (Pro) or phenylalanine (Phe) which may have a protected amino group.

A preferred amino acid residue which may have a protected carboxyl group in the Y is an α-carboxyalkyl($C_1$-$C_6$)amino group which may have a protected carboxyl group, still preferably a leucine (Leu) and a glycine (Gly) residue which may have a protected carboxyl group.

Examples of the peptide residue in the X or Y usually include oligopeptides comprising about 2 or 3 molecules of the above-described amino acids.

Typical examples of the peptide residue in the X include dipeptide residues such as Val-Val-, Val-Pro-, Val-Phe-, Phe-Val, Gly-Phe, Val-Thr-, Lys-Val- and Asp-Val- which may have a functional group, such as an amino group, protected.

Typical examples of the peptide residue in the Y include dipeptide residues such as -Leu-Val-OH and -Gly-Val-OH which may have a functional group, such as a carboxyl group, protected.

Examples of the amino-protective group (including not only the one in the X but also the ones in the amino acid residue and peptide residue) in the present invention include acyl groups including phthalyl and sulfonyl groups; and oxycarbonyl groups which protect the amino group by forming a urethane bond.

Examples of the acyl group include lower alkylcarbonyl groups having 1 to 6 carbon atoms (which may be substituted with a halogen, nitro, lower alkoxy, phenyl, etc.), benzoyl, phthalyl and arylsulfonyl groups. When the acyl group contains a phenyl group, the phenyl group may be substituted with a lower alkyl, halogen, lower alkoxy or nitro group.

Particular examples of the acyl group include substituted and unsubstituted hydrocarbon carbonyl groups having 1 to 9 carbon atoms, such as acetyl, trifluoroacetyl, phenylacetyl, propionyl, butanoyl, isopropionyl, isobutanoyl, dimethylbutanoyl, phenylbutanoyl, phenylpropionyl and benzoyl groups, among which hydrocarbon carbonyl groups having 4 to 8 carbon atoms are preferable.

Examples of the oxycarbonyl groups which protect the amino group by forming a urethane bond include unsubstituted lower alkoxycarbonyl and substituted lower alkyloxycarbonyl groups (the substituents being the same as those described above for the acyl groups), more particularly isopropyloxycarbonyl, t-butyloxycarbonyl, isopentyloxycarbonyl and benzyloxycarbonyl groups (which may be either substituted or unsubstituted, the substituents being the same as those described above for the acyl groups). A preferred group is benzyloxycarbonyl.

In addition to the above-described acyl groups and oxycarbonyl groups, benzyl, substituted benzyl (the substituents being the same as those described above), o-nitrophenylthio, triphenylmethyl and tosyl groups may be used as the protective group when occasion demands.

Y represents a peptide residue or amino acid residue in which the functional group may be protected. The peptide residues and amino acid residues of Y are the same as the peptide residues and amino acid residues of X. When Y represents a peptide or amino acid residue having a protected carboxyl group, the protective group for the carboxyl group includes ester-type protective groups (such as lower alkyl groups having 1 to 6 carbon atoms) which form lower alkyl esters having 1 to 6 carbon atoms (such as a methyl, ethyl, isopropyl, t-butyl, dimethylbutyl, or lower alkyl ester substituted with a phenyl group, e.g. a benzyl ester); and amide-type protective groups (such as a mono- or dialkylamino group having 1 to 6 carbon atoms, anilino or naphthylamino group) which form amides such as a mono- or di(lower alkyl($C_1$ to $C_6$))amide, e.g. methylamide, diethylamide, t-butylamide and i-butylamide, anilides and arylamides, e.g. naphthylamide.

E represents a substituent on the alkylene ($C_nH_{2n-1}$) selected from among halogens such as fluorine, chlorine, bromine and iodine, lower alkoxy groups having 1 to 6 carbon atoms (such as a methoxy, ethoxy, propoxy, butoxy or benzyloxy which is a substituted lower alkoxy) and hydrogen.

A represents a carbonyl group or mono- or di-substituted methylene (the substituent being a hydroxy, lower alkoxy, phenylimino or benzylimino). Examples of the substituted methylene group include hydroxymethylene, di(lower alkoxy)methylene, phenyliminomethylene and benzyliminomethylene groups. n is 2 to 6.

The symbols for the amino acid residues, protective groups, etc., as used herein are as follows:

Leu: leucine
Phe: phenylalanine
Val: valine
Ac: acetyl,
Boc: t-butyloxycarbonyl
t-Bu: t-butyl
Bzl: benzyl
Me: methyl
Ph: phenyl
Z: benzyloxycarbonyl Typical examples of the compounds of the formula (1) are given in the following table:

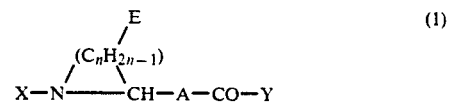

(1)

| Compound No. | X | n | E | A | Y |
|---|---|---|---|---|---|
| 1 | H—Val—Val | 3 | —H | —CO— | Leu—Val—OH |
| 2 | Z—Val—Val | " | " | " | " |
| 3 | Boc—Val—Val | " | " | " | " |
| 4 | Z—Val | " | " | " | " |
| 5 | Boc—Val | " | " | " | " |
| 6 | Z—Phe | " | " | " | " |
| 7 | Boc—Phe | " | " | " | " |
| 8 | Z | " | " | " | " |
| 9 | Boc | " | " | " | " |
| 10 | H | " | " | " | " |
| 11 | H—Val—Val | 4 | " | " | " |
| 12 | Z—Val—Val | " | " | " | " |
| 13 | Boc—Val—Val | " | " | " | " |
| 14 | Z—Val | " | " | " | " |
| 15 | Boc—Val | " | " | " | " |
| 16 | Z—Phe | " | " | " | " |
| 17 | Boc—Phe | " | " | " | " |
| 18 | Z | " | " | " | " |
| 19 | Boc | " | " | " | " |
| 20 | Ac | " | " | " | " |
| 21 | H—Val—Val | 3 | " | —CH(OH)— | " |
| 22 | Z—Val—Val | " | " | " | " |
| 23 | Boc—Val—Val | 3 | —H | —CH(OH)— | Leu—Val—OH |
| 24 | Z—Val | " | " | " | " |
| 25 | Boc—Val | " | " | " | " |
| 26 | Z—Phe | " | " | " | " |
| 27 | Boc—Phe | " | " | " | " |
| 28 | Z | " | " | " | " |
| 29 | Boc | " | " | " | " |
| 30 | Ac | " | " | " | " |
| 31 | H—Val—Val | 4 | " | " | " |
| 32 | Z—Val—Val | " | " | " | " |

-continued

| Compound No. | X | n | E | A | Y |
|---|---|---|---|---|---|
| 33 | Boc—Val—Val | " | " | " | " |
| 34 | Z—Val | " | " | " | " |
| 35 | Boc—Val | " | " | " | " |
| 36 | Z—Phe | " | " | " | " |
| 37 | Boc—Phe | " | " | " | " |
| 38 | Z | " | " | " | " |
| 39 | Boc | " | " | " | " |
| 40 | Ac | " | " | " | " |
| 41 | H—Val—Val | 3 | " | —CO— | Leu—Val—OBzl |
| 42 | Z—Val—Val | " | " | " | " |
| 43 | Boc—Val—Val | " | " | " | " |
| 44 | Z—Val | " | " | " | " |
| 45 | Boc—Val | 3 | —H | —CO— | Leu—Val—OBzl |
| 46 | Z—Phe | " | " | " | " |
| 47 | Boc—Phe | " | " | " | " |
| 48 | H | " | " | " | " |
| 49 | Boc | " | " | " | " |
| 50 | Ac | " | " | " | " |
| 51 | H—Val—Val | 4 | " | " | " |
| 52 | Z—Val—Val | " | " | " | " |
| 53 | Boc—Val—Val | " | " | " | " |
| 54 | Z—Val | " | " | " | " |
| 55 | Boc—Val | " | " | " | " |
| 56 | Z—Phe | " | " | " | " |
| 57 | Boc—Phe | " | " | " | " |
| 58 | Z | " | " | " | " |
| 59 | Boc | " | " | " | " |
| 60 | Ac | " | " | " | " |
| 61 | H—Val—Val | 3 | " | —CH(OH)— | " |
| 62 | Z—Val—Val | " | " | " | " |
| 63 | Boc—Val—Val | " | " | " | " |
| 64 | Z—Val | " | " | " | " |
| 65 | Boc—Val | " | " | " | " |
| 66 | Z—Phe | " | " | " | " |
| 67 | Boc—Phe | 3 | —H | —CH(OH)— | Leu—Val—OBzl |
| 68 | Z | " | " | " | " |
| 69 | Boc | " | " | " | " |
| 70 | Ac | " | " | " | " |
| 71 | H—Val—Val | 4 | " | " | " |
| 72 | Z—Val—val | " | " | " | " |
| 73 | Boc—Val—Val | " | " | " | " |
| 74 | Z—Val | " | " | " | " |
| 75 | Boc—Val | " | " | " | " |
| 76 | Z—Phe | " | " | " | " |
| 77 | Boc—Phe | " | " | " | " |
| 78 | Z | " | " | " | " |
| 79 | Boc | " | " | " | " |
| 80 | Ac | " | " | " | " |
| 81 | H—Val—Val | 3 | " | —CO— | Leu—O(t-Bu) |
| 82 | Z—Val—Val | " | " | " | " |
| 83 | Boc—Val—Val | " | " | " | " |
| 84 | Z—Val | " | " | " | " |
| 85 | Boc—Val | " | " | " | " |
| 86 | Z—Phe | " | " | " | " |
| 87 | Boc—Phe | " | " | " | " |
| 88 | Z | " | " | " | " |
| 89 | Boc | 3 | —H | —CO— | Leu—O(t-Bu) |
| 90 | Ac | " | " | " | " |
| 91 | H—Val—Val | 4 | " | " | " |
| 92 | Z—Val—Val | " | " | " | " |
| 93 | Boc—Val—Val | " | " | " | " |
| 94 | Z—Val | " | " | " | " |
| 95 | Boc—Val | " | " | " | " |
| 96 | Z—Phe | " | " | " | " |
| 97 | Boc—Phe | " | " | " | " |
| 98 | Z | " | " | " | " |
| 99 | Boc | " | " | " | " |
| 100 | Ac | " | " | " | " |
| 101 | Z—Val—Val | 3 | " | —C(OMe)$_2$— | " |
| 102 | Boc—Val—VAl | " | " | " | " |
| 103 | Z—Val | " | " | " | " |
| 104 | Boc—Val | " | " | " | " |
| 105 | Z—Phe | " | " | " | " |
| 106 | Boc—Phe | " | " | " | " |
| 107 | Z | " | " | " | " |
| 108 | Boc | " | " | " | " |
| 109 | Ac | " | " | " | " |
| 110 | Z—Val—Val | 4 | " | " | " |
| 111 | Boc—Val—Val | 4 | —H | —C(OMe)$_2$— | Leu—O(t-Bu) |
| 112 | Z—Val | " | " | " | " |
| 113 | Boc—Val | " | " | " | " |

-continued

| Compound No. | X | n | E | A | Y |
|---|---|---|---|---|---|
| 114 | Z—Phe | " | " | " | " |
| 115 | Boc—Phe | " | " | " | " |
| 116 | Z | " | " | " | " |
| 117 | Boc | " | " | " | " |
| 118 | Ac | " | " | " | " |
| 119 | Z—Val—Val | 3 | " | —C(=NPh)— | Leu—Val—OBzl |
| 120 | Boc—Val—Val | " | " | " | " |
| 121 | Z—Val | " | " | " | " |
| 122 | Boc—Val | " | " | " | " |
| 123 | Z—Phe | " | " | " | " |
| 124 | Boc—Phe | " | " | " | " |
| 125 | Z | " | " | " | " |
| 126 | Boc | " | " | " | " |
| 127 | Ac | " | " | " | " |
| 128 | Z—Val—Val | 4 | " | " | " |
| 129 | Boc—Val—Val | " | " | " | " |
| 130 | Z—Val | " | " | " | " |
| 131 | Boc—Val | " | " | " | " |
| 132 | Z—Phe | " | " | " | " |
| 133 | Boc—Phe | 4 | —H | —C(=NPh)— | Leu—Val—OBzl |
| 134 | Z | " | " | " | " |
| 135 | Boc | " | " | " | " |
| 136 | Ac | " | " | " | " |
| 137 | Boc | 3 | " | —CH(OH)— | Leu—O(t-Bu) |
| 138 | Boc | " | " | —CO— | " |
| 139 | (CH$_3$)$_3$CCH$_2$CO— | " | " | " | " |
| 140 | Z | " | " | " | " |
| 141 | Z—Phe | " | " | " | " |
| 142 | Z—Phe | " | " | " | Leu—OH |
| 143 | Boc | " | " | " | Leu—NH(t-Bu) |
| 144 | Z—Phe | " | " | " | " |
| 145 | Z—Pro | " | " | " | Leu—Val—OBzl |
| 146 | Z—Phe | " | " | " | Gly—O(t-Bu) |
| 147 | Z—Phe | " | " | " | Gly—OH |
| 148 | Z—Phe | " | " | " | Phe—O(t-Bu) |
| 149 | Z—Phe | " | " | " | Phe—OH | note:
The configuration of each of amino acids may be any of D, L or DL.

The compounds of the formula (1) in the present invention can be produced by an ordinary process employed in the field of peptide chemistry.

For example, they can be produced according to reaction schemes (A) and (B) given below.

Reaction scheme (A):

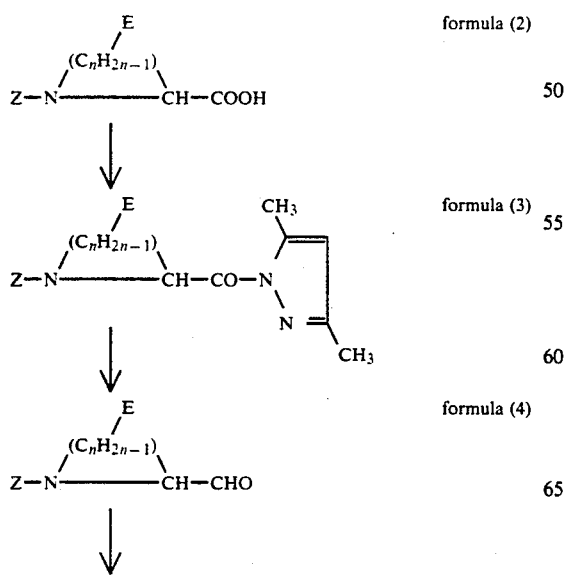

formula (2)

formula (3)

formula (4)

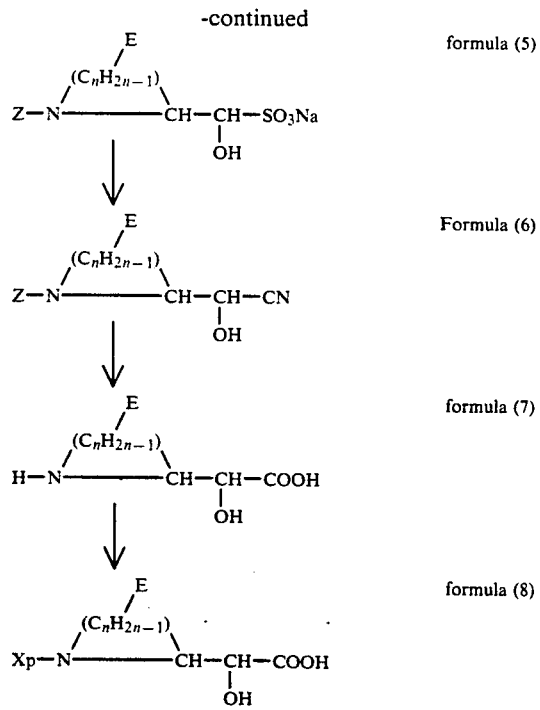

formula (5)

Formula (6)

formula (7)

formula (8)

In the above scheme, E is as defined above and Xp represents an amino-protective group. An example of the reaction scheme (A) is a reaction for forming α-(N-Boc-2-pyrrolidinyl)-α-hydroxyacetic acid from N-Z-proline (n is 3 and E is H in the above scheme) (wherein the configuration may be either L or DL) by a method described in literature [Rinzou Nishizawa and Tetsushi Saino, J. Med. Chem., 20, 513 (1977) or Japanese Patent Laid-Open No. 221667/1987]. Other intended α-hydroxyacetic acid derivatives can be obtained from the starting materials corresponding to the intended compounds by conducting the reaction by the process described in the above literature.

Reaction scheme (B):

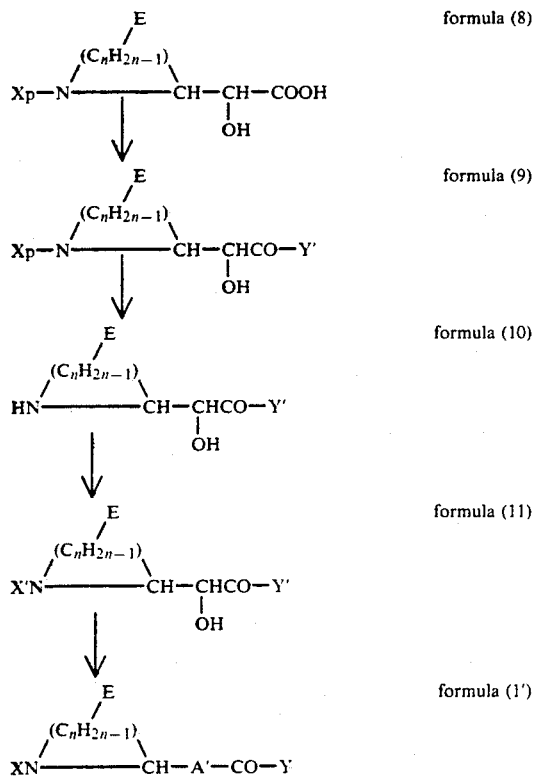

In the above scheme, E, Y and n are as defined above, A' is the same as A in the formula (1) except for hydroxymethine and X' is the same as X in the formula (1) except for hydrogen.

Detailed description will now be made on the steps of the reaction scheme (B).

A peptide of the formula (9) is produced by reacting an α-hydroxyacetic acid derivative of the formula (8) or its active ester with a compound of the formula H-Y' (Y' being an amino acid residue or peptide residue in which the carboxyl group is protected) in the presence of, if necessary, a peptide bond forming reagent such as dicyclohexylcarbodiimide and 1-hydroxybenzotriazole.

Then the amino-protective group (Xp) of the peptide of the formula (9) is removed to give a compound of the formula (10). The protective group (Xp) is removed by an ordinary process. For example, when the protective group is Boc, a protective group removing reagent such as a hydrochloric acid/dioxane solution or trifluoroacetic acid is used.

Then this compound is reacted with a compound of the formula X'—OH (X' being as defined above) to introduce X' thereinto, thereby forming a compound of the formula (11). When X' is an amino-protective group, the reaction is conducted by an ordinary process for introducing the protective group into the amino group, while when X' is an amino acid residue or peptide residue and the amino group is an unprotected one, the amino group is protected before X'—OH is reacted with the compound of the formula (10) in the same manner as that described above to form a peptide bond.

A compound of the formula (1') wherein A' represents a mono-(lower alkoxy)methylene can be produced by O-alkylating the compound of the formula (11) produced as described above with an alkylating agent such as methyl iodide, dimethylsulfate or benzyl bromide in the presence of a basic catalyst such as sodium hydride, potassium hydride or potassium carbonate and, if necessary, removing the protective group from the carboxyl group.

A compound of the formula (1') wherein A' represents a carbonyl group (—CO—) can be produced by oxidizing the hydroxyl group of the compound of the formula (11) with a combination of suitable oxidizing agents such as dimethyl sulfoxide (DMSO)/pyridine, trifluoroacetic acid/carbodiimide [dicyclohexyl carbodiimide, 1-ethyl-3-(3-dimethylaminopropyl)carbodiimide], and DMSO/acetic anhydride. The reaction is conducted usually in an inert organic solvent at a temperature ranging from −10° C. to the boiling point of the solvent.

A compound of the formula (1') wherein A' represents a di-(lower alkoxy)methylene can be produced by acetalizing a compound of the formula (1') wherein A' represents a carbonyl group with an orthoformate such as trimethyl orthoformate or triethyl orthoformate in the presence of a catalyst such as p-toluenesulfonic acid or Amberlyst 15.

A compound of the formula (1') wherein A represents an iminomethylene can be produced by reacting the carbonyl group with an amine compound such as aniline or benzylamine in the presence of a dehydrating reagent such as sodium sulfate, magnesium sulfate or molecular sieve.

If necessary, X or Y of the compound of the formula (1') can be exchanged with various groups by removing the protective group for X or Y of the compound of the formula (1') or by replacing the protective group by an ordinary process.

The second invention relates to an α-hydroxyacetic acid derivative of the formula (12). This compound is useful as an intermediate, since when the α-hydroxy group of the compound is oxidized, a new α-keto amide derivative of the formula (1) having a potent enzyme inhibiting effect can be obtained.

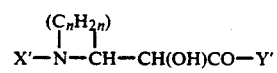

Formula (12):

wherein X', Y' and n are as defined above.

Experiments were conducted to evaluate the enzyme inhibiting activity of the compounds of the present invention by using prolyl endopeptidase as the enzyme model. They are given in the following Test Examples.

Test Example 1

Test Method

Method of Assaying Enzyme Inhibiting Activity

Benzyloxycarbonylglycylproline β-naphthylamide (0.1 mM) used as the substrate was reacted with prolyl endopeptidase obtained from porcine kidneys used as the enzyme in a 0.025 M tris(hydroxymethyl)methanamine hydrochloric acid solution (pH: 7.5) at 37° C.

reaction mixture for 30 min and then the absorbance of the product at 525 nm was measured. The inhibitory activity was expressed as the concentration necessary for 50% inhibition (IC$_{50}$).

The results are given in Table 1.

TABLE 1

| Enzyme inhibiting activity | IC$_{50}$ (μg/ml) |
|---|---|
| Compound of Example 7 | 0.0070 |
| Compound of Example 8 | 0.011 |
| Compound of Example 9 | 0.0024 |
| Compound of Example 14 | 0.009 |
| Compound of Example 15 | 0.046 |
| Compound of Example 16 | 0.0020 |
| Compound of Example 17 | 0.0013 |
| Compound of Example 19 | 0.0014 |
| Compound of Example 20 | 0.0022 |
| Compound of Example 21 | 0.0008 |
| Compound of Example 22 | 0.0011 |
| Compound of Example 23 | 0.0018 |

Thus the present invention serves to provide new α-keto amide derivatives of the formula (1) usable as the enzyme inhibitor having a specificity for enzymes or which are expected to have a prolyl endopeptidase inhibiting effect.

The following Examples will further illustrate the present invention, which by no means limit the invention. Unless otherwise stated, the configuration of each of the amino acids given in the Examples is L.

REFERENTIAL EXAMPLE 1

Synthesis of 2-hydroxy-2-(pyrrolidin-2-yl)acetic acid

N-Benzyloxycarbonyl-DL-proline (4.98 g) was dissolved in dry dichloromethane (100 ml) and 3,5-dimethylpyrazole (2.12 g) and dicyclohexylcarbodiimide (4.5 g) were added to the solution at −20° C. After 30 min the temperature was elevated to room temperature and the solution was stirred for 20 h. After the completion of the reaction, 0.3 ml of acetic acid was added to the reaction mixture and an insoluble matter was removed by filtration. After the solvent was distilled off, the residue was dissolved in a small amount of ethyl acetate. An insoluble matter was removed by filtration and the filtrate was evaporated to dryness under reduced pressure to give 6.0 g of N-benzyloxycarbonyl-DL-proline-3,5-dimethylpyrazolide (yield: 91.7%).

Lithium aluminum hydride (1.37 g) was suspended in anhydrous THF (20 ml) and the suspension was cooled to −20° C. A solution of N-benzyloxycarbonyl-DL-proline-3,5-dimethylpyrazolide (5.88 g) in anhydrous THF (45 ml) was added dropwise to the suspension for 30 min. After the completion of the addition, the reaction was continued at that temperature for 30 min. The reaction mixture was cooled to −60° C. and neutralized with hydrochloric acid. Celite was added to a precipitate thus formed and the mixture was filtered. The filtrate was concentrated and dissolved in ethyl acetate. After the organic layer was washed with a saturated aqueous sodium chloride solution, a solution of sodium hydrogensulfite (1.8 g) in 2 ml of water was added thereto and the mixture was concentrated. The residue was dissolved in 16 ml of water and ethyl acetate (32 ml) was added to the solution. An aqueous potassium cyanide solution (1.1 g/8 ml) was further added to the solution and stirred for 3 h.

Ethyl acetate (80 ml) was added to the reaction liquid, and the mixture was washed with a saturated aqueous sodium chloride solution and then with water, and dried over anhydrous sodium sulfate. Sodium sulfate was filtered off and the solvent was distilled off under reduced pressure to give an oily product, which was dissolved in concentrated hydrochloric acid (20 ml) and dioxane (20 ml) and the solution was refluxed for 10 h. The reaction liquid was concentrated under reduced pressure and the residue was washed with ether to give 1.14 g of 2-hydroxy-2-(pyrrolidin-2-yl)acetic acid hydrochloride (yield: 35.0%).

REFERENTIAL EXAMPLE 2

2-Hydroxy-2-(N-t-butyloxycarbonylpyrrolidin-2-yl)acetic acid

2-Hydroxy-2-(pyrrolidin-2-yl)acetic acid (520 mg) was dissolved in water (2 ml) and 1N NaOH (2.87 ml). Then a solution of di-t-butyl dicarbonate (940 mg) in 4 ml of dioxane was added to the solution under cooling with ice and the mixture was stirred at room temperature for 30 min. After continuing the stirring at room temperature for additional 5 h, ethyl acetate (30 ml) and a saturated aqueous sodium hydrogen-carbonate solution (30 ml) were added to the reaction mixture and an aqueous layer thus formed was separated. It was adjust to a pH value of 3 with phosphoric acid and extracted with ethyl acetate. The extract was dried over anhydrous sodium sulfate and filtered. The filtrate was concentrated to give oily 2-hydroxy-2-(N-t-butyloxycarbonylpyrrolidin-2-yl)acetic acid (800 mg) (52.0%).

$^1$H-NMR (CDCl$_3$)
δ: 1. 4 7, 1. 4 8 (S, S, 9H),
1. 7–2. 4 (m, 4H),
3. 3–3. 6 (m, 2H),
4. 1–4. 5 (m, 2H),
4.4–5. 2 (br, 2H)

EXAMPLE 1

[2-Hydroxy-2-(N-t-butyloxycarbonylpyrrolidin-2-yl)-acetyl]-D-leucylvaline benzyl ester 2-Hydroxy-2-(N-t-butyloxycarbonylpyrrolidin-2-yl)acetic acid (390 mg) was dissolved in dry dichloromethane (2 ml) and 1-hydroxybenzotriazole (200 mg) and dicyclohexylcarbodiimide (400 mg) were added to the solution under cooling with ice. A solution of D-leulcyl-L-valine benzyl ester trifluoroacetate (690 mg) in dichloromethane (2 ml) and triethylamine (330 μl) was added dropwise to the solution to conduct a reaction at room temperature for 20 h. The reaction liquid was concentrated and dissolved in ethyl acetate. The solution was washed with a 4% sodium hydrogencarbonate solution, a 1% aqueous citric acid solution and a saturated aqueous sodium chrolide solution. The organic layer was dried over anhydrous sodium sulfate and filtered. The filtrate was concentrated under reduced pressure to give 900 mg of an oily product, which was subjected to silica gel column chromatography and developed with a chloroform/acetone mixture (volume ratio: 15/1). A fraction containing the intended substance was concentrated under reduced pressure to give 590 mg of a white powder (yield: 67.7%).

$^1$H-NMR (CDCl$_3$)
δ: 0. 8–1. 0 (m, 1 2H),
1. 0–2. 4 (m, 1 8H),
3. 3–3. 5 (m, 2H),
3. 8–4. 2 (m, 2H),
4. 3–4. 6 (m, 2H),
5. 1 5 (d, 2H, J=2. 7 6 Hz),
6. 6–6. 9 (br, 2H), 7. 2–7. 4 (m, 5)

EXAMPLE 2

[2-Oxo-2-(N-t-butyloxycarbonylpyrrolidin-2-yl)acetyl]-D-leucylvaline benzyl ester Pyridine-trifluoroacetic acid (48.9 mg), 1-ethyl-3-(3-dimethylaminopropyl)carbodiimide hydrochloride (214 mg), DMSO (1.2 ml) and benzene (3 ml) were added to [2-hydroxy-2-(N-t-butyloxycarbonylpyrrolidin-2-yl)acetyl]-D-leucylvaline benzyl ester (190 mg) and the mixture was stirred at room temperature for 20 h. After the completion of the reaction, the reaction liquid was diluted with ethyl acetate (30 ml) and washed with water (10 ml). The ethyl acetate layer was dried over anhydrous sodium sulfate and filtered. The reaction liquid was concentrated. The resultant oily substance was subjected to silica gel column chromatography and developed with a chloroform/acetone (20/1) mixture and a fraction of the intended compound was concentrated to give 69.8 mg (yield: 36.9%) of a white powder.

$^1$H-NMR (CDCl$_3$)
δ: 0. 8–1. 0 (m, 1 2H),
1. 3–1. 5 (m, 9H),
1. 5–2. 5 (m, 9H),
3. 4–3. 6 (m, 2H),
4. 4–4. 6 (m, 2H),
5. 0–5. 3 (m, 3H),
6. 6–6. 8 (br, 1H),
7. 3–7. 4 (m, 5H).
FAB-MS
m/z: 5 4 6 (M$^+$+1)

EXAMPLE 3

[2-Hydroxy-2-(N-t-butyloxycarbonylpyrrolidin-2-yl)acetyl]-D-leucylvaline

[2-Oxo-2-(N-t-butyloxycarbonylpyrrolidin-2-yl)acetyl]-D-leucylvaline benzyl ester (30 mg) was dissolved in a mixture (5 ml) of acetic acid, methanol and water (1/1/1) and catalytic reduction was conducted in the presence of palladium black (5 mg) under hydrogen atmosphere for 2 h. The catalyst was filtered off and the filtrate was concentrated under reduced pressure to give 23 mg of colorless crystals (yield: 92%).

$^1$H-NMR (CD$_3$OD)
δ: 0. 8–1. 1 (m, 1 2H),
1. 2–2. 4 (m, 1 7H),
3. 4–3. 6 (m, 2H),
4. 2–4. 4 (m, 1H),
4. 5–4. 7 (m, 1H),
5. 0–5. 2 (m, 1H),
FAB-MS
m/z: 4 5 6 (M$^+$+1), 3 5 6

EXAMPLE 4

[2-Oxo-2-(pyrrolidin-2-yl)acetyl]-D-leucylvaline benzyl ester

[2-Oxo-2-(N-t-butyloxycarbonylpyrrolidin-2-yl)acetyl]-D-leucylvaline benzyl ester (30 mg) was dissolved in dichloromethane (0.5 ml) and a 4N hydrochloric acid/dioxane solution (0.5 ml) was added to the solution under cooling with ice to conduct a reaction at room temperature for 2 h. The reaction solution was concentrated under reduced pressure and the residue was washed with n-hexane several times and dried to give 21 m g (yield: 96.3%) of an oily substance.

$^1$H-NMR (CD$_3$OD)
δ: 0. 8–1. 1 (m, 1 2H),
1. 5–2. 3 (m, 8H),
3. 1–3. 4 (m, 2H),
3. 5–3. 9 (m, 1H),
4. 2–4. 4 (m, 1H),
4. 6–4. 8 (m, 1H),
5. 1 6 (s, 2H),
7. 3 6 (s, 5H).

EXAMPLE 5

[2-Oxo-2-(pyrrolidin 2-yl)acetyl]-D-leucylvaline

[2-Oxo-2-(N-t-butyloxycarbonylpyrrolidin-2-yl)acetyl]-D-leucylvaline (20 mg) was dissolved in dichloromethane (0.5 ml) and 4N hydrochloric acid/dioxane (0.5 ml) was added to the solution under cooling with ice to conduct a reaction at room temperature for 2 h. The reaction liquid was concentrated under reduced pressure and the residue was washed with n-hexane and concentrated to give 15 mg (yield: 94.9%) of colorless crystals.

$^1$H-NMR (CD$_3$OD)
δ: 0. 8–1. 1 (m, 1 2H),
1. 5–2. 3 (m, 8H),
3. 2–3. 4 (m, 2H),
3. 6–4. 0 (m, 1H),
4. 2–4. 5 (m, 1H),
4. 6–4. 8 (m, 1H),

EXAMPLE 6

N-Benzyloxycarbonyl-valylvalyl-[2-hydroxy-2-(pyrrolidin-2-yl)acetyl]-D-leucylvaline benzyl ester

[2-Hydroxy-2-(N-t-butyloxycarbonylpyrrolidin-2-yl)acetyl]-D-leucylvaline benzyl ester (200 mg) was added to dry dichloromethane (1 ml) and 4N hydrochloric acid/dioxane (1 ml) was added to the solution under cooling with ice to conduct a reaction at room temperature for 1.5 h. The reaction liquid was concentrated under reduced pressure and the residue was washed with n-hexane and dried to give 2-hydroxy-2-(pyrrolidin-2-yl)acetyl]-D-leucylvaline benzyl ester hydrochloride.

N-Benzyloxycarbonylvalylvaline (130 mg) was dissolved in dry dichloromethane (2 ml) and 1-hydroxybenzotriazole (62 mg) and dicyclohexyl-carbodiimide carbodiimide (92 mg) were added to the solution under cooling with ice. Then a solution of [2-hydroxy-2-(pyrrolidin-2-yl)acetyl]-D-leucylvaline benzyl ester (180 mg) in dry dichloromethane (2 ml) and triethylamine (78 μ) was added dropwise to the above mixture to conduct a reaction at room temperature for 20 h. The reaction liquid was concentrated under reduced pressure and dissolved in ethyl acetate. The solution was washed with a 5% aqueous sodium hydrogencarbonate solution, a 5% aqueous citric acid solution and a saturated aqueous sodium chloride solution. The ethyl acetate layer was dried over anhydrous sodium sulfate. After filtration, the filtrate was concentrated under reduced pressure to give 300 mg of an oily product, which was subjected to silica gel column chromatography and developed with a chloroform/acetone mixture (volume ratio: 15/1). A fraction containing the intended compound was concentrated under reduced pressure to give 200 mg (yield: 69.4%) of a white powder.

$^1$H-NMR (CD$_3$OD)
δ: 0. 8–1. 1 (m, 2 4H),
1. 2–2. 3 (m, 1 0H),
3. 5–4. 6 (m, 8H), 5. 0-4. 2 (m, 4H),
7. 3-7. 4 (m, 1 0H),

EXAMPLE 7

N-Benzyloxycarbonylvalylvalyl-[2-oxo-2-(pyrrolidin-2-yl)acetyl]-D-leucylvaline benzyl ester Pyridine-trifluoroacetic acid (44.4 mg), 1-ethyl-3-(3-dimethylaminopropyl)carbodiimide hydrochloride (44.4 mg), DMSO (1.11 ml) and benzene (3 ml) were added to N-benzyloxycarbonylvalylvalyl-[2-hydroxy-2-(pyrrolidin-2-yl)acetyl]-D-leucylvaline benzyl ester (245 mg) and the mixture was stirred at room temperature for 24 h. After the completion of the reaction, the reaction liquid was diluted with ethyl acetate (30 ml) and washed with water (5 ml). After being dried over anhydrous sodium sulfate followed by filtration, the reaction liquid was concentrated. An oily product thus obtained was subjected to silica gel chromatography and developed with a chloroform/acetone mixture (15/1). A fraction containing the intended compound was concentrated to give 180 mg (yield: 73.6%) of a white powder.

$^1$H-NMR (CD$_3$OD)
δ: 0. 8-1. 1 (m, 2 4H),
1. 6-2. 4 (m, 1 0H),
3. 6-4. 1 (m, 3H),
4. 3-4. 7 (m, 3H),
5. 0-5. 3 (m, 5H),
7. 2-7. 4 (m, 1 0H),
FAB-MS
m/z: 7 7 8 (M$^+$+1), 4 4 6

EXAMPLE 8

Valylvalyl-[2 oxo 2-(pyrrolidin-2-yl)acetyl]-D-leucylvaline

N-Benzyloxycarbonylvalylvalyl-[2-oxo-2-(pyrrolidin-2-yl)acetyl]-D-leucylvaline benzyl ester (180 mg) was dissolved in a mixture (5 ml) of acetic acid, methanol and water (1/1/1) and catalytic reduction was conducted in the presence of palladium black (30 mg) under hydrogen atmosphere for 3 h. The catalyst was removed by filtration and the filtrate was concentrated under reduced pressure to give 110 mg (yield: 85.9%) of colorless crystals.

$^1$H-NMR (CD$_3$OD)
δ: 0. 8-1. 2 (m, 2 4H),
1. 5-2. 4 (m, 1 0H),
3. 6-4. 0 (m, 3H),
4. 2-4. 7 (m, 3H),
5. 2-5. 4 (m, 1H),
FAB-MS
m/z: 5 5 4 (M$^+$+1)

EXAMPLE 9

N-Benzyloxycarbonylphenylalanyl-[2 hydroxy-2-(pyrrolidin-2-yl)acetyl]-D-leucylvaline benzyl ester

[2-Hydroxy-2-(N-t-butyloxycarbonylpyrrolidin-2-yl)acetyl]-D-leucylvaline benzyl ester (100 mg) was dissolved in dichloromethane (1 ml) and 1 ml of a 4N hydrochloric acid/dioxane solution was added to the solution under cooling with ice to conduct a reaction at room temperature for 2 h. The reaction liquid was concentrated under reduced pressure and the residue was washed with n-hexane several times and concentrated to give [2-hydroxy-2-(pyrrolidin-2-yl)acetyl]-D-leucylvaline benzyl ester hydrochloride.

Then N-benzyloxycarbonylphenylalanine (60.3 mg) was dissolved in dry dichloromethane (3 ml) and 1-hydroxybenzotriazole (36.8 mg) and dicyclohexylcarbodiimide (43.5 mg) were added to the solution under cooling with ice. Then a solution of [2-hydroxy-2-(pyrrolidin-2-yl)acetyl]-D-leucylvaline benzyl ester hydrochloride (88 mg) produced as described above in dichloromethane (2 ml) and triethylamine (40 μl) was added dropwise to the above solution and stirred for 20 h. The reaction liquid was concentrated and dissolved in ethyl acetate. The solution was washed with a 5% aqueous sodium hydrogencarbonate solution, a 5% aqueous citric acid solution and a saturated sodium chloride solution. An organic layer thus formed was dried over anhydrous sodium sulfate and filtered. The filtrate was concentrated under reduced pressure to give 120 mg of an oily substance, which was subjected to silica gel column chromatography and developed with a chloroform/acetone mixture (volume ratio: 20/1). A fraction containing the intended substance was concentrated to give 90 mg of a white powder (yield: 59.6%).

$^1$H-NMR (CD$_3$OD)
δ: 0. 8-1. 0 (m, 1 2H),
1. 1-2. 3 (m, 8H),
2. 8-3. 0 (m, 2H),
3. 3-3. 5 (m, 2H),
3. 9-4. 8 (m, 5H),
5. 0-5. 3 (m, 4H),
7. 1-7. 5 (m, 1 5H),
FAB-MS
m/z: 7 2 7 (M$^+$+1)

EXAMPLE 10

[2-Hydroxy-2-(N-t-butyloxycarbonylpiperidin-2-yl)-acetyl]-D-leucylvaline benzyl ester 2-Hydroxy-2-(N-t-butyloxycarbonylpiperidin-2-yl)acetic acid (88 mg) was dissolved in dry dichloromethane (3 ml) and 1-hydroxybenzotriazole (57 mg) and dicyclohexylcarbodiimide (84 mg) were added to the solution under cooling with ice. A solution of D-leucylvaline benzyl ester trifluoroacetate (148 mg) in dry dichloromethane (2 ml) and triethylamine (72 μl) was added dropwise to the solution under cooling with ice. The temperature was elevated to room temperature and the mixture was stirred for 20 h. The reaction liquid was concentrated and dissolved in ethyl acetate. The solution was washed with a 5% aqueous sodium hydrogencarbonate solution, a 5% aqueous citric acid solution and a saturated aqueous sodium chloride solution. The organic layer was dried over anhydrous sodium sulfate and filtered. The filtrate was concentrated to give 130 mg of an oily substance, which was subjected to silica gel column chromatography and developed with a chloroform/acetone mixture (volume ratio: 10/1). A fraction containing the intended substance was concentrated to give 95 mg of a white powder (yield: 49.7%).

$^1$H-NMR (CDCl$_3$)
δ:.0. 8-1. 0 (m, 1 2H),
1. 0-2. 3 (m, 1 9H),
3. 3-3. 6 (m, 2H),
3. 9-4. 2 (m, 2H),
4. 3-4. 6 (m, 3H),
4. 9-5. 3 (m, 3H),
6. 8-7. 0 (m, 1H),
7. 3 5 (s, 5H),

EXAMPLE 11

N-Benzyloxycarbonylvalylvalyl-[2-hydroxy-2-(piperidin-2-yl)acetyl]-D-leucylvaline benzyl ester

[2-Hydroxy-2-(N-t-butyloxycarbonylpiperidin-2-yl)acetyl]-D-leucylvaline benzyl ester (85 mg) was dissolved in dichloromethane (1 ml) and a 4N hydrochloric acid/dioxane solution (1 ml) was added to the solution under cooling with ice to conduct a reaction at room temperature for 2 h. The reaction liquid was concentrated under reduced pressure and the residue was washed with n-hexane several times and dried to give [2-hydroxy-2-(piperidin-2-yl)acetyl]-D-leucylvaline benzyl ester hydrochloride.

Then N-benzyloxycarbonylvalylvaline (52.6 mg) was dissolved in dry dichloromethane (2 ml) and 1-hydroxybenzotriazole (25.3 mg) and dicyclohexylcarbodiimide (37.1 mg) were added to the solution under cooling with ice. A solution of [2-hydroxy-2-(pyrrolidin-2-yl)acetyl]-D-leucylvaline benzyl ester hydrochloride in dry dichloromethane (1 ml) and triethylamine (32 μl) was added dropwise to the mixture and stirred for 20 h. The reaction liquid was concentrated and dissolved in ethyl acetate. The solution was washed with a 5% aqueous sodium hydrogencarbonate solution, a 5% aqueous citric acid solution and a saturated sodium chloride solution. An organic layer thus formed was dried over anhydrous sodium sulfate and filtered. The filtrate was concentrated to give 120 mg of an oily substance, which was subjected to silica gel column chromatography and developed with a chloroform/acetone mixture (volume ratio: 20/1). A fraction containing the intended substance was concentrated under reduced pressure to give 600 mg of a white powder (yield: 50.4%).

$^1$H-NMR (CD$_3$OD)
δ:0. 8–1. 0 (m, 2 4H),
1. 1–2. 3 (m, 1 2H),
3. 6–3. 8 (m, 4H),
3. 9–4. 4 (m, 2H),
4. 2–4. 4 (m, 2H),
5. 0–4. 2 (m, 4H),
7. 2–7. 4 (m, 1 0H),

EXAMPLE 12

[2-Hydroxy-2-(N-t-butyloxycarbonylpyrrolidin-2-yl)-acetyl]-D-leucine t-butyl ester 2-Hydroxy-2-[N-(t-butyloxycarbonyl)pyrrolidin-2-yl]acetic acid (180 mg), D-leucine t-butyl ester hydrochloride (83 mg) and triethylamine (74 μl) were dissolved in dry dichloromethane (3 ml) and 1-hydroxybenzotriazole (84 mg) and dicyclohexylcarbodiimide (109 mg) were added to the solution under cooling with ice. The temperature was elevated to room temperature and the stirring was conducted for 20 h. The reaction liquid was concentrated under reduced pressure and dissolved in ethyl acetate. The solution was washed with a saturated sodium hydrogencarbonate solution, a aqueous citric acid solution and a saturated aqueous sodium chloride solution. An ethyl acetate layer thus treated was dried over anhydrous sodium sulfate. After filtration, the filtrate was concentrated under reduced pressure, subjected to silica gel column chromatography and developed with a chloroform/acetone mixture (15:1). A fraction containing the intended substance was concentrated under reduced pressure to give 140 mg of a white powder (yield: 84.3%).

$^1$H-NMR (CDCl$_3$)
δ: 0. 9–1. 0 (m, 6H),
1.4–2. 5 (m, 2 5H),
3. 2–3. 6 (m, 2H),
3. 9–4. 6 (m, 3H),
6. 0–6. 3 (br, 2H),
7. 2–7. 4 (br, 1H)

EXAMPLE 13

[2-Oxo-2-(N-t-butyloxycarbonylpyrrolidin-2-yl)acetyl]-D-leucine t-butyl ester

Pyridine-trifluoroacetic acid (16.9 mg), dicyclohexylcarbodiimide (80 mg), DMSO (0.5 ml) and benzene (2 ml) were added to [2-hydroxy-2-(t-butyloxycarbonylpyrrolidin-2-yl)acetyl]-D-leucine t-butyl ester (48 mg) and the mixture was stirred at room temperature for 20 h. After the completion of the reaction, the reaction liquid was diluted with ethyl acetate (30 ml) and washed with water (10 ml). After drying over anhydrous sodium sulfate, the reaction liquid was concentrated. An oily product thus obtained was subjected to silica gel column chromatography and developed with a chloroform/acetone mixture (15/1). A fraction containing the intended compound was concentrated to give 30.0 mg (yield: 63%) of a white powder.

$^1$H-NMR (CDCl$_3$)
δ: 0. 9 5 (d, 6H, J=5. 6Hz)
1. 3–1. 5 (m, 1 8H),
1. 5–2. 5 (m, 7H),
3. 3–3. 7 (m, 2H),
4. 4–4. 6 (m, 1H),
5. 1–5. 3 (m, 1H),
7. 2–7. 4 (br, 1H)
FAB-MS m/z: 4 1 4 (M$^+$+1)

EXAMPLE 14

[2-Oxo-2-(N-(3,3-dimethylbutanoyl)pyrrolidin-2-yl)-acetyl]-D-leucine t-butyl ester A 1.5 N hydrochloric acid/dioxane solution (1.5 ml) was added to [2-hydroxy-2-(N-t-butyloxycarbonylpyrrolidin-2-yl)acetyl]-D-leucine t-butyl ester produced in Example (12) under cooling with ice and then a reaction was conducted at room temperature for 6 h. The reaction liquid was concentrated under reduced pressure and the residue was washed with n-hexane several times, dried, and dissolved in dry dichloromethane (1 ml). Triethylamine (16 μl), t-butylacetic acid (11 mg) and 1-hydroxybenzotriazole (16 mg) were added to the solution and then dicyclohexylcarbodiimide (21 mg) was added thereto under cooling with ice. The temperature was elevated to room temperature and the mixture was stirred for 20 h. The reaction liquid was concentrated under reduced pressure and dissolved in ethyl acetate. The solution was washed with a saturated aqueous sodium hydrogencarbonate solution, a 5% aqueous citric acid solution and a saturated sodium chloride solution. The ethyl acetate layer thus treated was dried over anhydrous sodium sulfate. After filtration, the filtrate was concentrated under reduced pressure and subjected to silica gel column chromatography and developed with a chloroform/acetone mixture (volume ratio: 15/1). A fraction containing the intended compound was concentrated under reduced pressure to give 27 mg of [2-hydroxy-2-(N-(3,3-dimethylbutanoyl))-pyrrolidin-2-yl)acetyl]-D-leucine t-butyl ester. Then pyridine-trifluoroacetic acid (9 mg), dicyclohexylcarbodiimide (43 mg), DMSO (0.3 ml) and benzene (1 ml) were added to the product to oxidize it in the same manner as that of Example (13) to give 21 mg of a purified white powder.

¹H-NMR (CDCl₃)
δ: 0.8 5-1. 0 (m, 6H)
1. 0 6 (s, 9H)
1. 4 6 (s, 9H)
1. 5-2. 4 (M, 9H)
3. 4-3. 8 (m, 2H)
4. 4-4. 6 (m, 1H)
5. 2-5. 5 (m, 1H)
7. 1-7. 4 (br, 1H)
FAB-MS m/z: 4 1 1 (M⁺+1)

EXAMPLE 15

[2-Oxo-2-(N-benzyloxycarbonylpyrrolidin-2-yl)acetyl]-D-leucine t-butyl ester

2-Hydroxy-2-(N-benzyloxycarbonylpyrrolidin-2-yl)-acetic acid (200 mg) produced in the same manner as that of Referential Example (2), D-leucine t-butyl ester hydrochloride (134 mg) and triethylamine (120 μl) were dissolved in dry dichloromethane (3 ml) and 1-hydroxybenzotriazole (136 mg) and dicyclohexylcarbodiimide (177 mg) were added to the solution under cooling with ice. The temperature was elevated to room temperature and the mixture was stirred for 20 h. The reaction liquid was concentrated under reduced pressure and dissolved in ethyl acetate. The solution was washed with a saturated aqueous sodium hydrogencarbonate solution, a 5% aqueous citric acid solution and a saturated aqueous sodium chloride solution. The ethyl acetate layer thus treated was dried over anhydrous sodium sulfate. After filtration, the filtrate was concentrated under reduced pressure, subjected to silica gel column chromatography and developed with a chloroform/acetone mixture (15/1). A fraction containing the intended compound was concentrated under reduced pressure to give 250 mg of [2-hydroxy-2-(N-benzyloxycarbonyl-pyrrolidin-2-yl)acetyl]-D-leucine t-butyl ester. Then 60 mg of this compound was dissolved in benzene (2 ml), oxidized with pyridine-trifluoroacetic acid (21 mg), dicyclohexylcarbodiimide (100 mg) and DMSO (0.5 ml) and purified in the same manner as that of Example (13) to give 42 mg of a white power.

¹H-NMR (CDCl₃)
δ: 0. 8 5-1. 0 (m, 6H)
1. 4-2. 1 (m, 1 5H)
2. 2-2. 5 (m, 1H)
3. 4-3. 7 (m, 2H)
4. 3-4. 6 (m, 1H)
5. 0-5. 4 (m, 3H)
7. 1-7. 5 (m, 6H)
FAB-MS m/z: 4 4 7 (M⁺+1)

EXAMPLE 16

N-Benzyloxycarbonylphenylalanyl-[2-oxo-2-(pyrrolidin-2-yl)acetyl]-D-leucin t-butyl ester:

190 mg of [2-hydroxy-2-(N-benzyloxycarbonylpyrrolidin-2-yl)acetyl]-D-leucine t-butyl ester produced in Example (15) was dissolved in a mixture of acetic acid, methanol and water (1/1/1) (10 ml) and reduced in the presence of palladium black under hydrogen atmosphere at room temperature for 6 h. The catalyst was filtered off and the filtrate was concentrated under reduced pressure to give 120 mg of a white powder. 97 mg of this compound was dissolved in dry dichloromethane (3 ml), and triethylamine (40 μl) and N-benzyloxycarbonyl-phenylalanine N-succinimide ester (97 mg) were added to the solution under cooling with ice. The temperature was elevated to room temperature and the mixture was stirred for 20 h. The reaction liquid was concentrated under reduced pressure and dissolved in ethyl acetate. The solution was washed with a saturated aqueous sodium hydrogencarbonate solution, a 5% aqueous citric acid solution and a saturated aqueous sodium chloride solution. The ethyl acetate layer thus treated was dried over anhydrous sodium sulfate. After filtration, the filtrate was concentrated under reduced pressure and subjected to silica gel chromatography and developed with a chloroform/acetone mixture (15/1). A fraction containing the intended compound was concentrated under reduced pressure to give 80 mg of N-benzyloxycarbonylphenylalanyl-[2-hydroxy-2-(pyrrolidin-2-yl)acetyl]-D-leucine t-butyl ester. Then 72 mg of this compound was dissolved in benzene (2 ml), oxidized with pyridine-trifluoroacetic acid (17 mg), dicyclohexylcarbodiimide (80 mg) and DMSO (0.5 ml) and purified in the same manner as that of Example (13) to give 53 mg of a white powder.

¹-NMR (CDCl₃)
δ: 0. 9 6 (d, 6H, J=5. 9Hz)
1. 2-1. 4 (m, 9H)
1. 4 6. 1. 4 7 (s, s, 9H)
2. 0-2. 4 (m, 7H)
2. 8-8. 7 (m, 4H)
4. 1-4. 4 (m, 1H)
4. 5-4. 8 (m, 1H)
5. 0-4. 1 (m, 1H)
5. 0-4. 1 (s, s, 2H)
5. 0 4, 4. 0 4 (s, s, 2H)
5. 1-5. 8 (m, 2H)
7. 1-7. 5 (m, 1 1H)
FAB-MS m/z: 5 9 4 (M⁺+1)

EXAMPLE 17

N-Benzyloxycarbonylphenylalanyl-[2-oxo-2-(pyrrolidin-2-yl)acetyl)-D-leucine

Trifluoroacetic acid (0.5 ml) was added to the compound (22 mg) produced in Example (16) and the mixture was stirred at room temperature for 1.5 h. The reaction liquid was concentrated under reduced pressure and the residue was washed with n-hexane several times and dried to give 17 mg of a white powder.

¹H-NMR (CDCl₃)
δ: 0. 8-1. 0 (m, 6H)
1. 4-2. 4 (m, 7H)
2. 7-3. 9 (m, 4H)
4. 0-4. 8 (m, 2H)
4. 9-5. 1 (m, 2H)
5. 1-6. 1 (m, & br 3H)
7. 1-7. 4 (m, 1 1H)
FAB-MS m/z: 5 3 8 (M⁺+1)

EXAMPLE 18

[2-Oxo-2-(N-t-butyloxycarbonylpyrrolidin-2-yl)acetyl]-D-leucine t-butylamide

2-Hydroxy-2-(N-t-butyloxycarbonylpyrrolidin-2-yl)acetic acid (137 mg) produced in Referential Example 2 was dissolved in dry dichloromethane (3 ml) and D-leucine t-butylamide hydrochloride (160 mg) and triethylamine (78 μl) were added to the solution. 1Hydroxybenzotriazole (95 mg) and dicyclohexylcarbodiimide (127 mg) were added to the mixture under cooling with ice. The temperature was elevated to room temperature and the mixture was stirred for 20 h. The reaction liquid was concentrated under reduced pressure and dissolved in ethyl acetate. The solution was washed with a saturated aqueous sodium hydrogencarbonate solution, a 5% aqueous citric acid solution and a saturated aqueous sodium chloride solution. The ethyl acetate layer thus treated was dried over anhydrous sodium sulfate. After filtration, the filtrate was concentrated under reduced pressure, subjected to silica gel column chromatography and developed with a chloroform/acetone mixture (15/1). A fraction containing the intended compound was concentrated under reduced pressure to give 180 mg of [2-hydroxy-2-(N-t-butyloxycarbonylpyrrolidin-2-yl)acetyl]-D-leucine t-butyl amide. Then 30 mg of this compound was dissolved in benzene (2 ml), oxidized with pyridine-trifluoroacetic acid (10 mg), dicyclohexylcarbodiimide (48 mg) and DMSO (0.5 ml) and purified in the same manner as that of Example (13) to give 21 mg of a white powder.

$^1$H-NMR (CDCl$_3$)

δ: 0. 94 (d, 6H, J=6. 1 Hz)
1. 35 & 1. 45 (s, s, 1 8H)
1. 5–2. 4 (m, 7H)
3. 4–3. 7 (m, 2H)
3. 9–4. 4 (m, 1H)
5. 1–4. 2 (m, 1H)
5. 5–6. 0 (br, 1H)
7. 1–7. 5 (br, 1H)
FAB-MS m/z: 4 1 2 (M$^{30}$ +1)

EXAMPLE 19

N-Benzyloxycarbonylphenylalanyl-[2-oxo-2-(pyrrolidin-2-yl)acetyl]-D-leucine t-butylamide

[2-Hydroxy-2-(N-t-butyloxycarbonylpyrrolidin-2-yl)acetyl]-D-leucine t-butylamide (144 mg) produced in the same manner as that of Example (18) was dissolved in dichloromethane (1 ml) and a 4N hydrochloric acid/dioxane solution (1 ml) was added to the solution under cooling with ice to conduct a reaction at room temperature for 2 h. The reaction solution was concentrated under reduced pressure and the residue was washed with n-hexane several times, dried and dissolved in dry dichloromethane (3 ml). Triethylamine (59 μl ) and N-benzyloxycarbonylphenylalanine N-succinimide ester (152 mg) were successively added to the solution. The temperature was elevated to room temperate and the mixture was stirred for 20 h. The reaction liquid was concentrated under reduced pressure and dissolved in ethyl acetate. The solution was washed with a saturated aqueous sodium hydrogencarbonate solution, a 5% aqueous citric acid solution and a saturated aqueous sodium chloride solution. The ethyl acetate layer thus treated was dried over anhydrous sodium sulfate. After filtration, the filtrate was concentrated under reduced pressure, subjected to silica gel column chromatography and developed with a chloroform/acetone mixture (30/1). A fraction containing the intended compound was concentrated under reduced pressure to give 178 mg of N-benzyloxycarbonylphenylalanyl[2-hydroxy-2-(pyrrolidin-2-yl)acetyl]-D-leucine t-butylamide. Then 148 mg of this compound was dissolved in benzene (4 ml), oxidized with pyridinetrifluoroacetic acid (35 mg), dicyclohexylcarbodiimide (164 mg) and DMSO (1 ml) and purified in the same manner as that of Example (13) to give 110 mg of a white powder.

$^1$H-NMR (CDCl$_3$)

δ: 0. 95 (d, 6H, J=6. 0Hz)
1. 35 (s, 9H)
1. 5–2. 4 (m, 7H)
2. 8–3. 7 (m, 4H)
4. 1–4. 4 (m, 1H)
4. 6–5. 8 (m, 1H)
5. 05 (s, s, 2H)
5. 2–5. 8 (m, 3H)
7. 2–7. 4 (m, 1 1H)
FAB-MS m/z: 5 9 3 (M$^+$ +1)

EXAMPLE 20

N-Benzyloxycarbonylprolyl-[2-oxo-2-(pyrrolidin-2-yl)acetyl]-D-leucylvaline benzyl ester

[2-Hydroxy-2-(N-t-butyloxycarbonylpyrrolidin-2-yl)acetyl]-D-leucylvaline benzyl ester (200 mg) produced in Example (1) was dissolved in dichloromethane (1 ml) and a 4N hydrochloric acid/dioxane solution (1 ml) was added to the solution under cooling with ice to conduct a reaction at room temperature for 2 h. The reaction liquid was concentrated under reduced pressure and the residue was washed with n-hexane several times, dried and dissolved in dry dichloromethane (3 ml).

Triethylamine (52 μl ) and N-benzyloxycarbonylproline N-succinimide ester (141 mg) were successively added to the solution. The temperature was elevated to room temperature and the mixture was stirred for 20 h. The reaction liquid was concentrated under reduced pressure and dissolved in ethyl acetate. The solution was washed with a saturated aqueous sodium hydrogencarbonate solution, a 5% aqueous citric acid solution and a saturated aqueous sodium chloride solution. The ethyl acetate layer thus treated was dried over anhydrous sodium sulfate. After filtration, the filtrate was concentrated under reduced pressure, subjected to silica gel column chromatography and developed with a chloroform/acetone mixture (30/1). A fraction containing the intended compound was concentrated under reduced pressure to give N-benzyloxycarbonylprolyl [2-hydroxy-2-(pyrrolidin-2-yl)acetyl]-D-leucylvaline benzyl ester (120 mg). Then 70 mg of this compound was dissolved in benzene (2 ml), oxidized with pyridine-trifluoroacetic acid (16 mg), dicyclohpxylcarbodiimide (180 mg) and DMSO (0.5 ml) and purified in the same manner as that of Example (13) to give 23 mg of a white powder.

$^1$H-NMR (CDCl$_3$)

δ: 0. 8–1. 0 (m, 1 2H)
1. 4–2. 3 (m, 1 2H)
3. 3–4. 1 (m, 4H)
4. 3–4. 6 (m, 3H)
4. 9–5. 3 (m, 5H)
6. 4–7. 5 (m, 1 2H)
FAB-MS m/z: 6 7 7 (M$^+$ +1)

EXAMPLE 21

N-Benzyloxycarbonylphenylalanyl-[2-oxo-2-(pyrrolidin-2-yl)acetyl]-glycine t-butyl ester 2-Hydroxy-2-(N-benzyloxycarbonylpyrrolidin-2-yl)acetic acid (163 mg) produced in the same manner as that of Referential Example (2), glycine t-butyl ester hydrochloride (103 mg) and triethylamine (98 μl ) were dissolved in dry dichloromethane (2 ml) and 1-hydroxybenzotriazole) (110 mg) and dicyclohexylcarbodiimide (144 mg) were added to the solution under cooling with ice. The temperature was elevated to room temperature and the mixture was stirred for 20 h. The reaction mixture was filtered and concentrated under reduced pressure and dissolved in ethyl acetate. The solution was washed with sodium hydrogencarbonate solution, a 5% aqueous citric acid solution and a saturated aqueous sodium chloride solution. The ethyl acetate layer thus treated was dried over anhydrous sodium sulfate. After filtration, the filtrate was concentrated under reduced pressure, subjected to silica gel column chromatography and developed with a chloroform/acetone mixture (15/1). A fraction containing the intended compound was concentrated under reduced pressure to give 200 mg of [2-hydroxy-2-(N-benzyloxycarbonylpyrrolidin-2-yl)acetyl]-glycine t-butyl ester. Then 231 mg of this compound was dissolved in methanol (10 ml) and catalytic reduction was conducted in the presence of palladium black under hydrogen atmosphere at room temperature for 6 h. The catalyst was removed by filtration and the filtrate was concentrated under reduced pressure to give 151 mg of white powder. The compound was dissolved in dry dichloromethane (2 ml) and N-benzyloxycarbonylphenylalanine N-hydroxysuccinimide ester (267 mg) were added to the solution under cooling with ice. The temperature was elevated to room temperature and the mixture was stirred for 20 h. The reaction mixture was concentrated under reduced pressure and dissolved in ethyl acetate. The solution was washed with a saturated aqueous sodium hydrogencarbonate solution, a 5% aqueous citric acid solution and a saturated aqueous sodium chloride solution. The ethyl acetate layer thus treated was dried over anhydrous sodium sulfate. After filtration, the filtrate was concentrated under reduced pressure and subjected to silica gel chromatography and developed with a chloroform/acetone mixture (15/1). A fraction containing the intended compound was concentrated under reduced pressure to give 265 mg of N-benzyloxycarbonylphenylalanyl-[2-hydroxy-2-(pyrrolidin-2-yl) acetyl]-glycine t-butyl ester. Then 133 mg of this compound was oxidized and purified in the same manner as that of Example (13) to give 78 mg of a white powder.

$^1$H-NMR (CDCl$_3$)
δ1. 49 (s, 9H)
1. 7–2. 4 (m, 4H)
2. 8–3. 7 (m, 4H)
3. 90, 4. 07 (dd, dd, 2H, J=18.4. 5.9Hz)
4. 5–4. 8 (m, 1H)
5. 04, 5. 05 (s, s, 2H)
5. 2–5. 7 (m, 2H)
7. 1–7. 5 (m, 1 1H)

EXAMPLE 22

N-Benzyloxycarbonylphenylalanyl-[2-oxo-2-(pyrrolidin-2-yl)acetyl]-glycine

Trifluoroacetric acid (0.5 ml) was added to the compound (33 mg) produced in Example (21) and the mixture was stirred at room temperature for 1.5 h. The reaction liquid was concentrated under reduced pressure and the residue was washed with n-hexane several times and dried to give 24 mg of a white powder.

$^1$H-NMR (CDCl$_3$)
δ1. 7–2. 4 (m, 4H)
2. 8–3. 85 (m, 4H)
3. 9–4. 2 (m, 2H)
4. 6–4. 8 (m, 1H)
5. 03, 5. 04 (s, s, 2H)
5. 2–5. 4 (m, 1H)
5. 9–5. 05 (m, 1H)
7. 1–7. 7 (m, 1 2H)

EXAMPLE 23

N-benzyloxycarbonylphenylalanyl-[2-oxo-2-(pyrrolidin-2-yl)acetyl]-leucine t-butyl ester 2-Hydroxy-2-(N-benzyloxycarbonylpyrrolidin-2-yl acetic acid (202 mg), leucine t-butyl ester hydrochloride (162 mg) and triethylamine (106 μl) were dissolved in dry dichloromethane (4 ml), and 1-hydroxybenzotriazole (196 mg) and 1-ethyl-3-(3-dimethylaminopropyl) carbodiimide hydrochloride (196 mg) were added to the solution under cooling with ice and stirred for 2 h. The temperature was elevated to room temperature and the mixture was stirred for 6 h. The reaction liquid was concentrated under reduced pressure and dissolved in ethyl acetate. The solution was washed with a 4% aqueous sodium hydrogencarbonate solution, a 5% aqueous citric acid solution and a saturated aqueous sodium chloride solution. The ethyl acetate layer thus treated was dried over anhydrous sodium sulfate. After filtration, the filtrate was concentrated under reduced pressure, purified with silica gel column chromatography and [2-hydroxy-2-(N-benzyloxycarbonylpyrrolidin-2-yl)acetyl]-leucine t-butyl ester (310 mg) was obtained. Then 310 mg of this compound was dissolved in methanol (10 ml) and catalytic reduction was conducted in the presence of palladium black under hydrogen atmosphere at room temperature for 6 h. The catalyst was filtered off and the filtrate was concentrated under reduced pressure to give 217 mg of a white powder. The obtained compound was dissolved in DMF (3 ml), and 1-benzyloxycarbonylphenylalanine (217 mg) and N-hydroxybenzotriazole (187 mg) were added to the solution. After 1-ethyl-3-(3-dimethylaminopropyl)-carbodiimide hydrochloride(185 mg) was added to this mixture under cooling with ice, the temperature was elevated to room temperature and the mixture was stirred for 5 h. The reaction liquid was dissolved in ethyl acetate. The solution was washed with a 4% aqueous sodium hydrogencarbonate solution, a 5% aqueous citric acid solution and a saturated aqueous sodium chloride solution. The ethyl acetate layer thus treated was dried over anhydrous sodium sulfate. After filtration, the filtrate was concentrated under reduced pressure, subjected to silica gel column chromatography and developed with a dichloromethane/methanol mixture (100/1). A fraction containing the intended compound was concentrated under reduced pressure to give N-benzyloxycarbonylphenylalanyl-[2-hydroxy-2-(pyrrodin-2-yl)acetyl]-leucine t-butyl ester (393 mg). Then 317 mg of this compound was oxidized with pyridinetrifuloroacetic acid (51 mg), dicyclohexylcarbodiimide (330 mg) and DMSO (4 ml) and purified in the same manner as that of Example (13) to give 265 mg of a white powder.

$^1$H-NMR (CDCl$_3$)
δ0. 87–1. 02 (m, 6H)
1. 48 (s, 9H)
1. 5–2. 05 (m, 6H)
2. 29 (m, 1H)
2. 90 (dd, 1H, J=1 4. 0, 7. 0 Hz)
3. 0–3. 2 (m, 2H)
3. 65 (m, 1H)
4. 69 (ddd, 1H, J=7. 0, 7. 0, 7. 0 Hz)
5. 02, 5. 06 (d, d, 2H, J=1 1.0, 1 1. 0 Hz)
5. 29 (dd, 1H J=9. 0. 5. 6 Hz)
5. 48 (br, 1H)
7. 1–7. 4 (m, 1 1H)

We claim:

1. A new α-keto amide derivative or a pharmaceutically acceptable salt thereof represented by the formula (1):

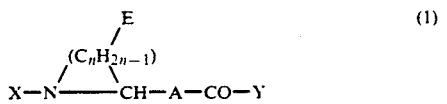

wherein X is selected from the group consisting of a branched $C_3$ to $C_6$ alkyl carbonyl, benzyloxycarbonyl-, benzyloxycarbonyl-Phe-, benzyloxycarbonyl-Pro-, H-Val-Val, benzyloxycarbonyl-Val-Val and t-butyloxycarbonyl; Y is selected from the group consisting of -Leu-OH, -Leu-NH(t-butyl), -Leu-O(t-butyl), -Gly-OH, -Gly-O(t-butyl, -Leu-Val-OH, -Leu-Val-OBenzyl, -Phe-O(t-butyl) and -Phe-OH; E represents a hydrogen atom; A represents a carbonyl group; and n represents an integer of 3.

2. A compound according to claim 1 wherein X represents $(CH_3)_3CCH_2CO-$ or benzyloxycarbonyl-Phe-.

3. A compound selected from among

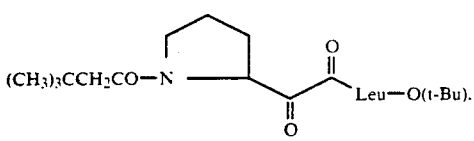

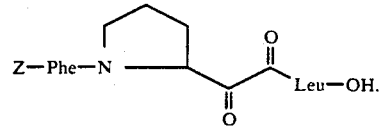

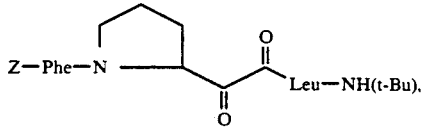

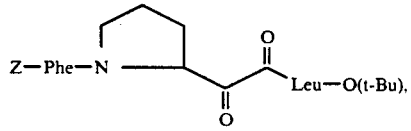

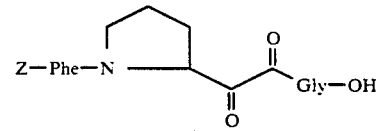

and

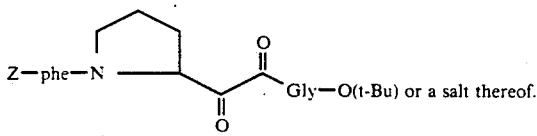

* * * * *